United States Patent

Yamamoto

[11] Patent Number: 6,166,036
[45] Date of Patent: Dec. 26, 2000

[54] LP(A)-LOWERING AGENT AND APOLIPOPROTEIN (A) FORMATION SUPPRESSING AGENT

[75] Inventor: Akira Yamamoto, Tokushima, Japan

[73] Assignee: Taiho Pharmaceutical Co., Ltd., Tokyo, Japan

[21] Appl. No.: 09/403,495

[22] PCT Filed: Feb. 23, 1999

[86] PCT No.: PCT/JP99/00798

§ 371 Date: Oct. 22, 1999

§ 102(e) Date: Oct. 22, 1999

[87] PCT Pub. No.: WO99/43318

PCT Pub. Date: Sep. 2, 1999

[30] Foreign Application Priority Data

Feb. 24, 1998 [JP] Japan ................... 10-042004

[51] Int. Cl.[7] .......... A61K 31/40; A61K 31/445
[52] U.S. Cl. .......... 514/321; 514/424; 546/197; 548/551
[58] Field of Search ............. 548/551; 546/197; 514/321, 424

[56] References Cited

U.S. PATENT DOCUMENTS

| | | | |
|---|---|---|---|
| 5,145,865 | 9/1992 | Fujii et al. | 514/424 |
| 5,231,184 | 7/1993 | Stokbroekx | 546/209 |
| 5,475,118 | 12/1995 | Yano et al. | 548/551 |

FOREIGN PATENT DOCUMENTS

| | | |
|---|---|---|
| 3-275666 | 12/1991 | Japan . |
| 4-112868 | 4/1992 | Japan . |
| 94/06767 | 3/1994 | WIPO . |

OTHER PUBLICATIONS

Watanabe et al., Eur. J. Med. Chem., 1994, 29, 675–686.

*Primary Examiner*—Fiona T. Powers
*Attorney, Agent, or Firm*—Sughrue, Mion, Zinn, Macpeak & Seas, PLLC

[57] ABSTRACT

Described is an Lp(a) lowering agent or an apo(a) formation suppressing agent, which comprises as an effective ingredient a phenylcarboxylic acid derivative represented by the following formula (1):

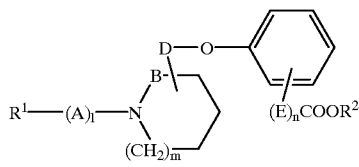

(wherein, $R^1$ represents a phenyl group which may have a substituent, A represents a lower alkylene or lower alkyleneoxy group, B represents a methylene or carbonyl group, D represents a lower alkylene group, E represents a lower alkylene or lower alkenylene group, $R^2$ represents a hydrogen atom or a lower alkyl group and 1, m and n each stands for 0 or 1), or salt thereof. The agent is capable of lowering the blood level of Lp(a) significantly while hardly causing side effects.

13 Claims, No Drawings

LP(A)-LOWERING AGENT AND APOLIPOPROTEIN (A) FORMATION SUPPRESSING AGENT

TECHNICAL FIELD

The present invention relates to an Lp(a) lowering agent and an apolipoprotein (a) formation suppressing agent each comprising as an effective ingredient a specific phenylcarboxylic acid derivative or salt thereof.

BACKGROUND ART

Lp(a) is a kind of lipoproteins. It is considered that apolipoprotein (a) (apo (a)) is attached, by an S—S bond, to apo B-100 which surrounds molecules analogous to low density lipoprotein (LDL), thereby circularly surrounding the particles (refer to Arteriosclerosis, 24(7·8), 369–374 (1996)). As a result of investigation continued since the existence of Lp(a) was reported [Acta. Pathol. Microbiol. Scand., 59, 369–382(1963)], Lp(a) is presumed to participate in the onset of ischemic cardiac diseases or cerebral infarction. When a patient has suffered from hyperlipoproteinemia of Lp(a) in spite of being free from a factor of hypercholesterolemia, diabetes, hypertension or the like, the onset ratio of an arteriosclerotic disease is rec ognized to become markedly as one of risk factors which may cause arteriosclerosis. For example, it is reported that when the total cholesterol level in blood is normal but the Lp(a) level is high, the onset ratio of a coronary artery disease becomes high (New England J. Med., 322(1990)). In addition, it is known that the level of Lp(a) is high in Buerger's disease which is a non-arteriosclerotic lesion, which suggests the relation between them [Arteriosclerosis, 24(7·8), 369–374 (1996)]. In most cases, occurrence of hyperlipoproteinemia of Lp(a) has been found to be governed by the genetic character of the patient.

In recent years, Lp(a) is found to have a fundamental structure similar to that of plasminogen and is therefore presumed to participate in the suppression of the coagulation fibrinolytic system, thus having thrombus forming action [Nature, 330, 132–137(1987)]. In addition, Lp(a) is presumed to participate in the constriction of an injured tissue in the lumen of a blood vessel by inhibiting activation of TGF-β and accelerating the proliferation of endothelial cells within the blood vessel and migration of smooth muscle cells from the media into the inner membrane [J. Cell. Biol., 113, 1439–1445(1991)].

From such findings, there was a demand for the development of an agent capable of significantly lowering the Lp(a) level in blood as a remedy or preventive for arteriosclerotic diseases free from a factor of hypercholesterolemia, diabetes, hypertension or the like, a remedy or preventive for Buerger's disease, and also as anti-thrombosis and a remedy or preventive for reconstriction after PTCA.

Most of the conventional anti-hyperlipidemia agents are reported to have no apparent effects for lowering the Lp(a) level in blood. Only a nicotinic acid derivative is regarded to be effective (ARTERIOSCLEROSIS, 10(5), 672–679 (1990)), but it is insufficient as a pharmaceutical, because administration at a high dose (1.5 to 2.0 g/body) is required owing to its markedly weak action and in addition, side effects such as suffusion appear.

An object of the present invention is therefore to provide an Lp(a) lowering agent which can significantly lower the Lp(a) level, is almost free from side effects and exhibits effects at a low dose. Another object of the present invention is to provide an agent for suppressing the formation of apo(a) which constitutes such Lp(a).

DISCLOSURE OF THE INVENTION

With a view to attaining the above-described objects, the present inventors have carried out an extensive investigation. As a result, paying attention to phenylcarboxylic acid derivatives and salts thereof each of which has a specific structure and is known to inhibit synthesis of cholesterol or fatty acid, the present inventors have found that such phenylcarboxylic acid derivatives and salts thereof are capable of significantly lowering the level of Lp(a), are almost free from side effects and exhibit effects at a low dose. They have also found that such derivatives and salts thereof are capable of suppressing the production of apo(a) which constitutes Lp(a), and completed the present invention.

In one aspect of the present invention, there is thus provided an Lp(a) lowering agent or apo(a) formation suppressing agent comprising as an effective ingredient a phenylcarboxylic acid derivative represented by the following formula (1):

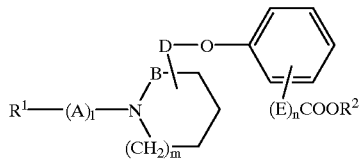

(wherein, $R^1$ represents a phenyl group which may have a substituent, A represents a lower alkylene or lower alkyleneoxy group, B represents a methylene or carbonyl group, D represents a lower alkylene group, E represents a lower alkylene or lower alkenylene group, $R^2$ represents a hydrogen atom or a lower alkyl group and l, m and n each stands for 0 or 1), or salt thereof.

In another aspect of the present invention, there is also provided the use of a phenylcarboxylic acid derivative represented by the above-described formula (1) or salt thereof for the preparation of an Lp(a) lowering agent or apo(a) formation suppressing agent.

In a further aspect of the present invention, there is also provided a method of treating a patient having a high Lp(a) or apo(a) level in blood, which comprises administering a phenylcarboxylic acid derivative represented by the above-described formula (1) or salt thereof.

BEST MODES FOR CARRYING OUT THE INVENTION

The phenylcarboxylic acid derivatives or salts thereof to be used as an effective ingredient in the present invention have already been disclosed in Japanese Patent Application Laid-Open No. Hei 3-275666 and International Application Laid-Open No. WO94/06767. Although they are known to have fatty acid synthesis inhibitory action and cholesterol synthesis inhibitory action, it is utterly unknown that such phenylcarboxylic acid derivatives or salts thereof are useful as an Lp(a) lowering agent and apo(a) formation suppressing agent having excellent Lp(a) lowering action and apo(a) formation suppressing action.

In the formula (1), examples of the substituent for the phenyl group, as $R^1$, which may have a substituent include halogen atoms, lower alkyl groups, cycloalkyl groups, a hydroxyl group, lower alkoxyl groups, phenoxy groups each having a halogen atom or a lower alkyl group as a substituent, a carboxyl group, lower alkylsulfonyloxy groups, phenylsufonyloxy groups each of which may have a halogen atom as a substituent, (lower)alkylsulfonyloxy (lower)alkoxyl groups, an amino group, lower alkanoylamino groups, a benzoylamino group, lower alkenyloxy groups, phenyl(lower)alkoxy(lower)alkoxyl groups, hydroxy(lower)alkoxyl groups, phenyl(lower)alkoxyl groups each of which may have, on the phenyl ring thereof, one to three groups selected from the class consisting of halogen atoms, lower alkyl groups and lower alkoxyl groups, halogen-substituted lower alkyl groups, $C_{3-8}$ cycloalkyloxy groups each of which may have a hydroxyl group as a substituent, ($C_{3-8}$ cycloalkyl)-substituted lower alkoxyl groups each of which may have, at the cycloalkyl moiety thereof, a hydroxyl group as a substituent, imidazolyl (lower)alkyl groups, imidazolyl(lower)alkoxyl groups and lower alkylenedioxy groups.

Examples of the halogen atom include fluorine, chlorine, bromine and iodine atoms.

Examples of the lower alkyl group include linear or branched $C_{1-6}$ alkyl groups such as methyl, ethyl, n-propyl, isopropyl, n-butyl, isobutyl, tert-butyl, pentyl and hexyl.

Examples of the cycloalkyl group include $C_{3-8}$ cycloalkyl groups such as cyclopropyl, cyclobutyl, cyclopentyl, cyclohexyl, cycloheptyl and cyclooctyl.

Examples of the lower alkoxyl group include linear or branched $C_{1-6}$ alkoxyl groups such as methoxy, ethoxy, n-propoxy, isopropoxy, n-butoxy, tert-butoxy, pentyloxy and hexyloxy.

Examples of the phenoxy group having a halogen atom or a lower alkyl group as a substituent include phenoxy groups each having, on the phenyl ring thereof, a halogen atom as a substituent, such as 2-chlorophenoxy, 3-chlorophenoxy, 4-chlorophenoxy, 2-fluorophenoxy, 3-fluorophenoxy, 4-fluorophenoxy, 2-bromophenoxy, 3-bromophenoxy, 4-bromophenoxy, 2-iodophenoxy, 3-iodophenoxy and 4-iodophenoxy; and phenoxy groups each having, on the phenyl group thereof, a $C_{1-6}$ alkyl group as a substituent, such as 2-methylphenoxy, 3-methylphenoxy, 4-methylphenoxy, 2-ethylphenoxy, 3-propylphenoxy, 4-isopropylphenoxy, 4-tert-butylphenoxy, 2-pentylphenoxy, 3-hexylphenoxy and 4-hexylphenoxy.

Examples of the lower alkylsulfonyloxy group include a sulfonyloxy group having one of the above-exemplified lower alkyl groups as a substituent.

Examples of the phenylsulfonyloxy group which may have a halogen atom as a substituent include a phenylsulfonyloxy group which may be substituted by 1 to 3 halogen atoms.

Examples of the (lower)alkylsulfonyloxy(lower)alkoxyl group include lower alkoxyl groups each having one of the above-exemplified lower alkylsulfonyloxy groups as a substituent.

Examples of the lower alkanoylamino group include amino groups each having a $C_{2-6}$ alkanoyl groups, such as acetylamino, propionylamino, butyrylamino, pentanoylamino and hexanoylamino.

Examples of the lower alkenyloxy group include $C_{2-6}$ alkenyloxy groups such as vinyloxy, allyloxy, 1-propenyloxy, butenyloxy, pentenyloxy and hexenyloxy.

Examples of the phenyl(lower)alkoxy(lower)alkoxyl group include lower alkoxyl groups each having a phenyl (lower)alkoxyl group, such as phenylmethoxymethoxy, 1-phenylmethoxyethoxy, 2-phenylmethoxypropoxy, 4-phenylmethoxybutoxy, 5-phenylmethoxypentyloxy, 6-phenylmethoxyhexyloxy, 1-phenylethoxymethoxy, 1-phenylethoxyethoxy and 2-phenylethoxypropoxy.

Examples of the hydroxy(lower)alkoxyl group include linear or branched $C_{1-6}$ alkoxyl groups each having 1 to 3 hydroxyl groups as a substituent, such as hydroxymethoxy, 2-hydroxyethoxy, 2-hydroxypropoxy, 2-hydroxyisopropoxy, 4-hydroxybutoxy, 2-hydroxy-tert-butoxy, 5-hydroxypentyloxy, 6-hydroxyhexyloxy, 1,2-dihydroxypropoxy, 1,2,3-trihydroxybutoxy and 1,1,4-trihydroxybutoxy.

Examples of the phenyl(lower)alkoxyl group which may have, on the phenyl ring thereof, 1 to 3 groups selected from the class consisting of halogen atoms, lower alkyl groups and lower alkoxyl groups include unsubstituted phenylalkoxyl groups each having, as an alkoxyl moiety, a linear or branched $C_{1-6}$ alkoxyl group, such as benzyloxy, 2-phenylethoxy, 3-phenyipropoxy, 4-phenylbutoxy, 1,1-dimethyl-2-phenyl-butoxy, 5-phenylpentyloxy and 6-phenylhexyloxy; and phenylalkoxyl groups each having, on the phenyl ring thereof, 1 to 3 substituents selected from the class consisting of halogen atoms, linear or branched $C_{1-6}$ alkyl groups and linear or branched $C_{1-6}$, alkoxyl groups and having, as an alkoxyl moiety, a linear or branched $C_{1-6}$ alkoxyl group, such as 2-chlorobenzyloxy, 3-chlorobenzyloxy, 4-chlorobenzyloxy, 2-bromobenzyloxy, 3-bromobenzyloxy, 4-bromobenzyloxy, 2-fluorobenzyloxy, 3-fluorobenzyloxy, 4-fluorobenzyloxy, 2-iodobenzyloxy, 3-iodobenzyloxy, 4-Iodobenzyloxy, 2-methylbenzyloxy, 3-methylbenzyloxy, 4-methylbenzyloxy, 2-ethylbenzyloxy, 3-propylbenzyloxy, 4-isopropylbenzyloxy, 4-tert-butylbenzyloxy, 2-pentylbenzyloxy, 3-hexylbenzyloxy, 2-(2-chlorophenyl)ethoxy, 3-(4-bromophenyl)propoxy, 1,1-dimethyl-2-(3-fluorophenyl)butoxy, 6-(4-chlorophenyl) hexyloxy, 2-(4-ethylphenyl)ethoxy, 3-(2-methylphenyl) propoxy, 2-(4-tert-butylphenyl)hexyloxy, 6-(tert-butylphenyl)hexyloxy, 6-(4-hexylphenyl)hexyloxy, 4-methoxybenzyloxy, 2-ethoxybenzyloxy, 3-propyloxybenzyloxy, 4-isopropyloxybenzyloxy, 4-tert-butyloxybenzyloxy, 2-pentyloxybenzyloxy, 3-hexyloxybenzyloxy, 2-(2-methoxyphenyl)ethoxy, 3-(4-methoxyphenyl)propoxy, 2-(4-ethoxyphenyl)ethoxy, 3-(2-methoxyphenyl)propoxy, 2-(4-tert-butoxyphenyl)hexyloxy, 6-(4-tert-butoxyphenyl)hexyloxy and 6-(4-hexyloxyphenyl) hexyloxy.

Examples of the halogen-substituted lower alkyl group include lower alkyl groups each having 1 to 3 halogen atoms as a substituent.

Examples of the $C_{3-8}$ cycloalkyloxy group which may have a hydroxyl group as a substituent include $C_{3-8}$ cycloalkyloxy groups each having 1 to 3 hydroxyl groups as a substituent, such as hydroxycyclopropyloxy, 1-hydroxycyclobutyloxy, 1-hydroxycyclopentyloxy, 1-hydroxycyclohexyloxy, 1,2-dihydroxycyclohexyloxy, 1,2,3-trihydroxycyclohexyloxy, 1-hydroxycycloheptyloxy and 1-hydroxycyclooctyloxy.

Examples of the ($C_{3-8}$ cycloalkyl)-substituted lower alkoxyl groups each of which may have, at the cycloalkyl moiety thereof, a hydroxyl group as a substituent include lower alkoxyl groups substituted by one of the above-exemplified $C_{3-8}$ cycloalkyl groups each having 1 to 3 hydroxyl groups as a substituent.

Examples of the imidazolyl(lower)alkyl group include linear or branched $C_{1-6}$ alkyl groups each having an imidazolyl group as a substituent, such as imidazolylmethyl, 1-(1-imidazolyl)ethyl, 2-(1-imidazolyl)propyl, 2-(2-imidazolyl)isopropyl, 3-(1-imidazolyl)butyl, 3-(2- imidazolyl)isobutyl, 2-(1-imidazolyl)-tert-butyl, 5-(1-imidazolyl)pentyl and 6-(1-imidazolyl)hexyl.

Examples of the imidazolyl(lower)alkoxyl group include linear or branched $C_{1-6}$ alkoxyl groups each having an imidazolyl group as a substituent, such as imidazolylmethoxy, 1-(1-imidazolyl)ethoxy, 2-(1-imidazolyl)propoxy, 2-(2-imidazolyl)isopropyloxy, 3-(1-imidazolyl)butoxy, 3-(2-imidazolyl)isobutyloxy, 2-(1-imidazolyl)-tert-butyloxy, 5-(1-imidazolyl)pentyloxy and 6-(1-imidazolyl)hexyloxy.

Examples of the lower alkylenedioxy group include $C_{1-4}$ alkylenedioxy groups such as methylenedioxy, ethylenedioxy, trimethylenedioxy and tetramethylenedioxy.

Among them, the lower alkyl groups and cycloalkyl groups are preferred, with the lower alkyl groups being more preferred and the tert-butyl group being particularly preferred. Such a substituent can be bonded to any one of the carbon atoms at the 2 to 6 positions of the phenyl group in any number of the substituents from 1 to 5, with the bonding only to the 4-position being particularly preferred.

In the formula (1), A represents a lower alkylene or lower alkyleneoxy group. Examples of the lower alkylene group include linear or branched, $C_{1-6}$ alkylene groups such as methylene, ethylene, trimethylene, tetramethylene, pentamethylene, hexamethylene, 2,2-dimethyltrimethylene, 2-methyltrimethylene and methylmethylene. Examples of the lower alkyleneoxy group include linear or branched $C_{1-6}$ alkyleneoxy groups such as methyleneoxy, ethyleneoxy, trimethyleneoxy, tetramethyleneoxy, pentamethyleneoxy, hexamethyleneoxy, 2,2-dimethyltrimethyleneoxy, 2-methyltrimethyleneoxy and methylmethyleneoxy. 1 stands for 0 or 1, with 0 being preferred.

B represents a methylene or carbonyl group, of which the carbonyl group is preferred. m stands for 0 or 1, with 0 being preferred. D represents a lower alkylene group and examples of it are similar to those exemplified as A, with the methylene group being preferred. D may be bonded to any one of the carbon atoms at the 3-, 4- and 5-positions in the below-described formula (2) in the formula (1):

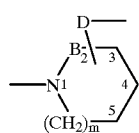

(2)

(wherein B and m have the same meanings as described above), with the bonding to the carbon atom at the 4-position being particularly preferred. E represents a lower alkylene or lower alkenylene group. Examples of the lower alkylene groups are similar to those exemplified as A, while those of the lower alkenylene group include linear or branched, $C_{2-6}$ alkenylene groups such as vinylene, propenylene, 1-methylvinylene, 2-butenylene, 3-pentenylene and 2-hexenylene. n stands for 0 or 1, with 0 being preferred.

In the formula (1), $R^2$ represents a hydrogen atom or a lower alkyl group. Examples of the lower alkyl group are similar to those exemplified above. As $R^2$, a hydrogen atom or a methyl group is preferred. To any one of the carbon atoms at the 2 to 6-positions of the phenyl group, the group $(E)_n COOR^2$ can be bonded in any number of the groups from 1 to 5, with the bonding only to the 4-position being particularly preferred.

In the formula (2), the carbon atom at the 3-, 4- or 5-position to which D is bonded is an asymmetric carbon atom so that the phenylcarboxylic acid derivative represented by the formula (1) has an optical isomer. In the present invention, R-form and S-form, and a mixture of them can be embraced.

Among the phenylcarboxylic acid derivatives represented by the formula (1), compounds having a basic group can be converted easily into acid addition salts thereof by acting a pharmaceutically-acceptable acid on the compounds. Examples of such an acid include inorganic acids such as hydrochloric acid, sulfuric acid, phosphoric acid and hydrobromic acid; and organic acids such as oxalic acid, maleic acid, fumaric acid, malic acid, tartaric acid, citric acid, benzoic acid, acetic acid, p-toluenesulfonic acid and ethanesulfonic acid. On the other hand, compounds having an acidic group, among the phenylcarboxylic acid derivatives represented by the formula (1), can be converted easily into salts thereof by acting a pharmaceutically acceptable basic compound on the compounds. Examples of such a basic compound include metal hydroxides such as sodium hydroxide, potassium hydroxide and calcium hydroxide; and alkali metal carbonates and alkali metal bicarbonates such as sodium carbonate and potassium bicarbonate.

Specific examples of the component of the present invention include compounds as described in Japanese Patent Application Laid-Open No. Hei 3-275666 and International Application Laid-Open No. WO94/06767, such as 1-(4-tolyl)-5-oxo-3-pyrrolidinecarboxylic acid, methyl 1-(4-fluorophenyl)-5-oxo-3-pyrrolidinecarboxylate, 1-(4-fluorophenyl)-4-hydroxymethyl-2-pyrrolidone, methyl 4-[1-(4-fluorophenyl)-2-pyrrolidon-4-yl]methoxybenzoate, 4-[1-(4-fluorophenyl)-2-pyrrolidon-4-yl]methoxybenzoic acid, methyl 1-(4-chlorophenyl)-5-oxo-3-pyrrolidinecarboxylate, 1-(4-chlorophenyl)-4-hydroxymethyl-2-pyrrolidone, methyl 4-[1-(4-chlorophenyl)-2-pyrrolidon-4-yl]methoxybenzoate, 4-[1-(4-chlorophenyl)-2-pyrrolidon-4-yl]methoxybenzoic acid, methyl 1-(3-chlorophenyl)-5-oxo-3-pyrrolidinecarboxylate, 1-(3-chlorophenyl)-4-hydroxymethyl-2-pyrrolidone, methyl 4-[1-(3-chlorophenyl)-2-pyrrolidon-4-yl]methoxybenzoate, 4-[1-(3-chlorophenyl)-2-pyrrolidon-4-yl]methoxybenzoic acid, methyl 1-(2-chlorophenyl)-5-oxo-3-pyrrolidinecarboxylate, 1-(2-chlorophenyl)-4-hydroxymethyl-2-pyrrolidone, methyl 4-[1-(2-chlorophenyl)-2-pyrrolidon-4-yl]methoxybenzoate, 4-[1-(2-chlorophenyl)-2-pyrrolidon-4-yl]methoxybenzoic acid, methyl 1-phenyl-5-oxo-3-pyrrolidinecarboxylate, 1-phenyl-4-hydroxymethyl-2-pyrrolidone, methyl 4-(1-phenyl-2-pyrrolidon-4-yl)methoxybenzoate, 4-(1-phenyl-2-pyrrolidon-4-yl)methoxybenzoic acid, 1-(4-n-propylphenyl)-5-oxo-3-pyrrolidinecarboxylic acid, methyl 1-(4-n-propylphenyl)-5-oxo-3-pyrrolidinecarboxylate, 1-(4-n-propylphenyl)-4-hydroxymethyl-2-pyrrolidone, methyl 4-[1-(4-n-propylphenyl)-2-pyrrolidon-4-yl]methoxybenzoate, 4-[1-(4-n-propylphenyl)-2-pyrrolidon-4-yl]methoxybenzoic acid, 1-(4-n-butylphenyl)-5-oxo-3-pyrrolidinecarboxylic acid, methyl 1-(4-n-butylphenyl)-5-oxo-3-pyrrolidinecarboxylate, 1-(4-n-butylphenyl)-4-hydroxymethyl-2-pyrrolidone, methyl 4-[1-(4-n-butylphenyl)-2-pyrrolidon-4-yl]methoxybenzoate, 4-[1-(4-n-butylphenyl)-2-pyrrolidon-4-yl]methoxybenzoic acid, 1-(4-tert-butylphenyl)-5-oxo-3-pyrrolidinecarboxylic acid, methyl 1-(4-tert-butylphenyl)-5-oxo-3-pyrrolidinecarboxylate, 1-(4-tert-butylphenyl)-4-hydroxymethyl-2-pyrrolidone, methyl 4-[1-(4-tert-butylphenyl)-2-pyrrolidon-4-yl]methoxybenzoate, 4-[1-(4-tert-butylphenyl)-2-pyrrolidon-4-yl]methoxybenzoic acid, 1-(4-n-pentylphenyl)-5-oxo-3-pyrrolidinecarboxylic acid, methyl 1-(4-n-pentylphenyl)-5-oxo-3- pyrrolidinecarboxylate, 1-(4-n-pentylphenyl)-4-hydroxymethyl-2-pyrrolidone, methyl 4-[1-(4-n-pentylphenyl)-2-pyrrolidon-4-yl]methoxybenzoate, 4-[1-(4-n-pentylphenyl)-2-pyrrolidon-4-yl]methoxybenzoic acid, 1-(4-n-hexylphenyl)-5-oxo-3-pyrrolidinecarboxylic acid, methyl 1-(4-n-hexylphenyl)-5-oxo-3-pyrrolidinecarboxylate, 1-(4-n-hexylphenyl)-4-hydroxymethyl-2-pyrrolidone, methyl 4-[1-(4-n-hexylphenyl)-2-pyrrolidon-4-yl]methoxybenzoate, 4-1-(4-n-hexylphenyl)-2-pyrrolidon-4-ylmethoxybenzoic acid, 1-(4-cyclohexylphenyl)-5-oxo-3-pyrrolidinecarboxylic acid, methyl 1-(4-cyclohexylphenyl)-5-oxo-3-pyrrolidinecarboxylate, 1-(4-cyclohexylphenyl)-4-hydroxymethyl-2-pyrrolidone, methyl 4-[1-(4-cyclohexylphenyl)-2-pyrrolidon-4-yl]methoxybenzoate, 4-[1-(4-cyclohexylphenyl)-2-pyrrolidon-4-yl]methoxybenzoic acid, 1-(4-methoxyphenyl)-5-oxo-3-pyrrolidinecarboxylic acid, methyl 1-(4-methoxyphenyl)-5-oxo-3-pyrrolidinecarboxylate, 1-(4-methoxyphenyl)-4-hydroxymethyl-2-pyrrolidone, methyl 4-[1-(4-methoxyphenyl)-2-pyrrolidon-4-yl]methoxybenzoate, 4-[1-(4-methoxyphenyl)-2-pyrrolidon-4-yl]methoxybenzoic acid, 1-(4-n-butoxyphenyl)-5-oxo-3-pyrrolidinecarboxylic acid, methyl 1-(4-n-butoxyphenyl)-5-oxo-3-pyrrolidinecarboxylate, 1-(4-n-butoxyphenyl)-4-hydroxymethyl-2-pyrrolidone, methyl 4-[1-(4-n-butoxyphenyl)-2-pyrrolidon-4-yl]methoxybenzoate, 4-[1-(4-n-butoxyphenyl)-2-pyrrolidon-4-yl]methoxybenzoic acid, 1-[4-(4-chlorophenoxy)phenyl]-5-oxo-3-pyrrolidinecarboxylic acid, methyl 1-[4-(4-chlorophenoxy)phenyl]-5-oxo-3-pyrrolidinecarboxylate, 1-[4-(4-chlorophenoxy)phenyl]-4-hydroxymethyl-2-pyrrolidone, methyl 4-[1-[4-(4-chlorophenoxy)phenyl]-2-pyrrolidon-4-yl]methoxybenzoate, 4-[1-[4-(4-chlorophenoxy)phenyl]-2-pyrrolidon-4-yl]methoxybenzoic acid, 1-(3,4-methylenedioxyphenyl)-5-oxo-3-pyrrolidinecarboxylic acid, methyl 1-(3,4-methylenedioxyphenyl)-5-oxo-3-pyrrolidinecarboxylate, 1-(3,4-methylenedioxyphenyl)-4-hydroxymethyl-2-pyrrolidone, methyl 4-[1-(3,4-methylenedioxyphenyl)-2-pyrrolidon-4-yl]methoxybenzoate, 4-[1-(3,4-methylenedioxyphenyl)-2-pyrrolidon-4-yl)]methoxybenzoic acid, methyl 1-(3,4-dichlorophenyl)-5-oxo-3-pyrrolidinecarboxylate, 1-(3,4-dichlorophenyl)-4-hydroxymethyl-2-pyrrolidone, methyl 4-[1-(3,4-dichlorophenyl)-2-pyrrolidon-4-yl]methoxybenzoate, 4-[1-(3,4-dichlorophenyl)-2-pyrrolidon-4-yl]methoxybenzoic acid, 1-(5-chloro-2-methoxyphenyl)-5-oxo-3-pyrrolidinecarboxylic acid, methyl 1-(5-chloro-2-methoxyphenyl)-5-oxo-3-pyrrolidinecarboxylate, 1-(5-chloro-2-methoxyphenyl)-4-hydroxymethyl-2-pyrrolidone, methyl 4-[1-(5-chloro-2-methoxyphenyl)-2-pyrrolidon-4-yl]methoxybenzoate, 4-[1-(5-chloro-2-methoxyphenyl)-2-pyrrolidon-4-yl]methoxybenzoic acid, 1-(4-chloro-2-methylphenyl)-5-oxo-3-pyrrolidinecarboxylic acid, methyl 1-(4-chloro-2-methylphenyl)-5-oxo-3-pyrrolidinecarboxylate, 1-(4-chloro-2-methylphenyl)-4-hydroxymethyl-2-pyrrolidone, methyl 4-[1-(4-chloro-2-methylphenyl)-2-pyrrolidon-4-yl]methoxybenzoate, 4-[1-(4-chloro-2-methylphenyl)-2-pyrrolidon-4-yl]methoxybenzoic acid, 1-(3,5-dimethylphenyl)-5-oxo-3-pyrrolidinecarboxylic acid, methyl 1-(3,5-dimethylphenyl)-5-oxo-3-pyrrolidinecarboxylate, 1-(3,5-dimethylphenyl)-4-hydroxymethyl-2-pyrrolidone, methyl 4-[1-(3,5-dimethylphenyl)-2-pyrrolidon-4-yl]methoxybenzoate, 4-[1-(3,5-dimethylphenyl)-2-pyrrolidon-4-yl]methoxybenzoic acid, 1-(2,5-dimethylphenyl)-5-oxo-3-pyrrolidinecarboxylic acid, methyl 1-(2,5-dimethylphenyl)-5-oxo-3-pyrrolidinecarboxylate, 1-(2,5-dimethylphenyl)-4-hydroxymethyl-2-pyrrolidone, methyl 4-[1-(2,5-dimethylphenyl)-2-pyrrolidon-4-yl]methoxybenzoate, 4-[1-(2,5-dimethylphenyl)-2-pyrrolidon-4-yl]methoxybenzoic acid, 1-(2,4-dimethylphenyl)-5-oxo-3-pyrrolidinecarboxylic acid, methyl 1-(2,4-dimethylphenyl)-5-oxo-3-pyrrolidinecarboxylate, 1-(2,4-dimethylphenyl)-4-hydroxymethyl-2-pyrrolidone, methyl 4-[1-(2,4-dimethylphenyl)-2-pyrrolidon-4-yl]methoxybenzoate, 4-[1-(2,4-dimethylphenyl)-2-pyrrolidon-4-yl]methoxybenzoic acid, 1-(4-ethylphenyl)-5-oxo-3-pyrrolidinecarboxylic acid, 1-(4-ethylphenyl)-4-hydroxymethyl-2-pyrrolidone, methyl 4-[1-(4-ethylphenyl)-2-pyrrolidon-4-yl]methoxybenzoate, 4-[1-(4-ethylphenyl)-2-pyrrolidon-4-yl]methoxybenzoic acid, 1-(4-bromophenyl)-4-hydroxymethyl-2-pyrrolidone, methyl 4-[1-(4-bromophenyl)-2-pyrrolidon-4-yl]methoxybenzoate, 4-[1-(4-bromophenyl)-2-pyrrolidoin-4-yl]methoxybenzoic acid, 1-(4-isopropylphenyl)-5-oxo-3-pyrrolidinecarboxylic acid, 1-(4-isopropylphenyl)-4-hydroxymethyl-2-pyrrolidone, methyl 4-[1-(4-isopropylphenyl)-2-pyrrolidon-4-yl]methoxybenzoate, 4-[1-(4-isopropylphenyl)-2-pyrrolidon-4-yl]methoxybenzoic acid, 1-(4-ethoxycarbonylphenyl)-5-oxo-3-pyrrolidinecarboxylic acid, 1-(4-ethoxycarbonylphenyl)-4-hydroxymethyl-2-pyrrolidone, methyl 4-[1-(4-ethoxycarbonylphenyl)-2-pyrrolidon-4-yl]methoxybenzoate, 4 -[1-(4-carboxyphenyl)-2-pyrrolidon-4-yl]methoxybenzoic acid, 1-(4-hydroxyphenyl)-5-oxo-3-pyrrolidinecarboxylic acid, methyl 1-(4-hydroxyphenyl)-5-oxo-3-pyrrolidinecarboxylate, methyl 1-(4-ethoxyphenyl)-5-oxo-3-pyrrolidinecarboxylate, 1-(4-ethoxyphenyl)-4-hydroxymethyl-2-pyrrolidone, methyl 4-[1-(4-ethoxyphenyl)-2-pyrrolidon-4-yl]methoxybenzoate, 4-[1-(4-ethoxyphenyl)-2-pyrrolidon-4-yl]methoxybenzoic acid, methyl 1-(4 -n-propoxyphenyl)-5-oxo-3-pyrrolidinecarboxylate, 1-(4-n-propoxyphenyl)-4-hydroxymethyl-2-pyrrolidone, methyl 4-[1-(4-n-propoxyphenyl)-2-pyrrolidon-4-yl]methoxybenzoate, 4-[1-(4-n-propoxyphenyl)-2-pyrrolidon-4-yl]methoxybenzoic acid, methyl 1-(4-isopropoxyphenyl)-5-oxo-3-pyrrolidinecarboxylate, 1-(4-isopropoxyphenyl)-4-hydroxymethyl-2-pyrrolidone, methyl 4-[1-(4-isopropoxyphenyl)-2-pyrrolidon-4-yl]methoxybenzoate, 4-[1-(4-isopropoxyphenyl)-2-pyrrolidon-4-yl] methoxybenzoic acid, methyl 1-(4-benzyloxyphenyl)-5-oxo-3-pyrrolidinecarboxylate, 1-(4-benzyloxyphenyl)-4-hydroxymethyl-2-pyrrolidone, methyl 4-[1-(4-benzyloxyphenyl)-2-pyrrolidon-4-yl]methoxybenzoate, 4-[1-(4-benzyloxyphenyl)-2-pyrrolidon-4-yl] methoxybenzoic acid, methyl 1-[4-(4-chlorobenzyloxy)phenyl]-5-oxo-3-pyrrolidinecarboxylate, 1-[4-(4-chlorobenzyloxy)phenyl]-4-hydroxymethyl-2-pyrrolidone, methyl 4-[1-[4-(4-chlorobenzyloxy)phenyl]-2-pyrrolidon-4-yl]methoxybenzoate, 4-[1-[4-(4-chlorobenzyloxy)phenyl]-2-pyrrolidon-4-yl]methoxybenzoic acid, methyl 1-[4-(4-isopropylbenzyloxy)phenyl]-5-oxo-3-pyrrolidinecarboxylate, 1-[4-(4-isopropylbenzyloxy)phenyl]-4-hydroxymethyl-2-pyrrolidone, methyl 4-[1-[4-(4-isopropylbenzyloxy)phenyl]-2-pyrrolidon-4-yl]methoxybenzoate, 4-[1-[4-(4-isopropylbenzyloxy)phenyl]-2-pyrrolidon-4-yl]methoxybenzoic acid, methyl 1-[4-(4-tert-butylbenzyloxy)phenyl]-5-oxo-3-pyrrolidinecarboxylate, 1-[4-(4-tert-butylbenzyloxy)phenyl]-4-hydroxymethyl-2-pyrrolidone, methyl 4-[1-[4-(4-tert-butylbenzyloxy)phenyl]-2-pyrrolidon-4-yl]methoxybenzoate, 4-[1-[4-(4-tert-butylbenzyloxy)phenyl]-2-pyrrolidon-4-yl]methoxybenzoic acid, methyl 4-[1-(4- hydroxyphenyl)-2-pyrrolidon-4-yl]methoxybenzoate, 4-[1-(4-hydroxyphenyl)-2-pyrrolidon-4-yl]methoxybenzoic acid, methyl 4-[1-(4-chlorophenyl)-2-pyrrolidon-4-yl]methoxycinnamate, 4-[1-(4-chlorophenyl)-2-pyrrolidon-4-yl]methoxycinnamic acid, methyl 4-[1-(4-chlorophenyl)-2-pyrrolidon-4-yl]methoxy-α-methylcinnamate, 4-[1-(4-chlorophenyl)-2-pyrrolidon-4-yl]methoxy-α-methylcinnamic acid, methyl 3-[4-[1-(4-chlorophenyl)-2-pyrrolidon-4-yl]methoxy]phenylpropionate, 3-[4-[1-(4-chlorophenyl)-2-pyrrolidon-4-yl]methoxy]phenylpropionic acid, methyl 3-[4-[1-(4-chlorophenyl)-2-pyrrolidon-4-yl]methoxy]phenyl-2-methylpropionate, 3-[4-[1-(4-chlorophenyl)-2-pyrrolidon-4-yl]methoxy]phenyl-2-methylpropionic acid, methyl 2-[1-(4-chlorophenyl)-2-pyrrolidon-4-yl]methoxybenzoate, 2-[1-(4-chlorophenyl)-2-pyrrolidon-4-yl]methoxybenzoic acid, methyl 3-[1-(4-chlorophenyl)-2-pyrrolidon-4-yl]methoxybenzoate, 3-[1-(4-chlorophenyl)-2-pyrrolidon-4-yl]methoxybenzoic acid, 1-(4-chlorobenzyl)-5-oxo-3-pyrrolidinecarboxylic acid, methyl 1-(4-chlorobenzyl)-5-oxo-3-pyrrolidinecarboxylate, 1-(4-chlorobenzyl)-4-hydroxymethyl-2-pyrrolidone, methyl 4-[1-(4-chlorobenzyl)-2-pyrrolidon-4-yl]methoxybenzoate, 4-[1-(4-chlorobenzyl)-2-pyrrolidon-4-yl]methoxybenzoic acid, 1-(3,5-di-tert-butyl-4-hydroxyphenyl)-5-oxo-3-pyrrolidinecarboxylic acid, methyl 1-(3,5-di-tert-butyl-4-hydroxyphenyl)-5-oxo-3-pyrrolidinecarboxylate, 1-(3,5-di-tert-butyl-4-hydroxyphenyl)-4-hydroxymethyl-2-pyrrolidone, methyl 4-[1-(3,5-di-tert-butyl-4-hydroxyphenyl)-2-pyrrolidon-4-yl]methoxybenzoate, 4-[1-(3,5-di-tert-butyl-4-hydroxyphenyl)-2-pyrrolidon-4-yl]methoxybenzoic acid, 1-(4-chlorophenyl)-6-oxo-3-piperidinecarboxylic acid, 1-(4-chlorophenyl)-5-hydroxymethyl-2-piperidone, methyl 4-[1-(4-chlorophenyl)-2-piperidon-5-yl]methoxybenzoate, 4-[1-(4-chlorophenyl)-2-piperidon-5-yl]methoxybenzoic acid, 1-(4-chlorophenyl)-4-cyanomethyl-2-pyrrolidone, methyl 1-(4-chlorophenyl)-5-oxopyrrolidin-3-ylacetate, 1-(4-chlorophenyl)-4-(2-hydroxyethyl)-2-pyrrolidone, methyl 4-[2-[1-(4-chlorophenyl)-2-pyrrolidon-4-yl]ethoxybenzoate, 4-[2-[1-(4-chlorophenyl)-2-pyrrolidon-4-yl]ethoxy]benzoic acid, ethyl 1-(3,4-methylenedioxyphenoxyacetyl)piperidine-4-carboxylate, 1-[2-(3,4-methylenedioxyphenoxy)ethyl]-4-hydroxymethylpiperidine, methyl 4-[1-[2-(3,4-methylenedioxyphenoxy)ethyl]piperidin-4-yl]methoxybenzoate, 4-[1-[2-(3,4-methylenedioxyphenoxy)ethyl]piperidin-4-yl]methoxybenzoic acid, ethyl 1-(piperonyloyl)piperidine-4-carboxylate, 1-piperonyl-4-hydroxymethylpiperidine, methyl 4-(1-piperonylpiperidin-4-yl)methoxybenzoate, 4-(1-piperonylpiperidin-4-yl)methoxybenzoic acid, ethyl 1-(piperonyloyl)piperidine-3-carboxylate, 3-hydroxymethyl-1-piperonylpiperidine, methyl 4-(1-piperonylpiperidin-3-yl)methoxybenzoate, 4-(1-piperonylpiperidin-3-yl)methoxybenzoic acid, ethyl 1-(3,4-methylenedioxyphenylacetyl)piperidine-3-carboxylate, 1-[2-(3,4-methylenedioxyphenyl)ethyl]-3-hydroxymethylpiperidine, methyl 4-[1-[2-(3,4-methylenedioxyphenyl)ethyl]piperidin-3-yl]methoxybenzoate, 4-[1-[2-(3,4-methylenedioxyphenyl)ethyl]piperidin-3-yl]methoxybenzoic acid, ethyl 1-(3,4-methylenedioxyphenylacetyl)piperidine-4-carboxylate, 1-[2-(3,4-methylenedioxyphenyl)ethyl]-4-hydroxymethylpiperidine, methyl 4-[1-[2-(3,4-methylenedioxyphenyl)ethyl]piperidin-4-yl]methoxybenzoate, 4-[1-[2-(3,4-methylenedioxyphenyl)ethyl]piperidin-4-yl]methoxybenzoic acid, ethyl 1-(4-tert-butylbenzoyl)piperidine-3-carboxylate, 1-(4-tert-butylbenzyl)-3-hydroxymethylpiperidine, methyl 4-[1-(4-tert-butylbenzyl)piperidin-3-yl]methoxybenzoate, 4-[1-(4-tert-butylbenzyl)piperidin-3-yl]methoxybenzoic acid, ethyl 1-(4-chlorobenzoyl)piperidine-3-carboxylate, 1-(4-chlorobenzyl)-3-hydroxynethylpiperidine, methyl 4-[1-(4-chlorobenzyl)piperidin-3-yl]methoxybenzoate, 4-[1-(4-chlorobenzyl)piperidin-3-yl]methoxybenzoic acid, 1-(4-chlorophenyl)-3-hydroxymethylpyrrolidine, methyl 4-[1-(4-chlorophenyl)pyrrolidin-3-yl]methoxybenzoate, 4-[1-(4-chlorophenyl)pyrrolidin-3-yl]methoxybenzoic acid, 1-(4-tert-butylphenyl)-3-hydroxymethylpyrrolidine, methyl 4-[1-(4-tert-butylphenyl)pyrrolidin-3-yl]methoxybenzoate, 4-[-(4-tert-butylphenyl)pyrrolidin-3-yl]methoxybenzoic acid, 1-[4-(4-tert-butylphenoxy)phenyl]-5-oxo-3-pyrrolidinecarboxylic acid, 1-[4-(4-tert-butylphenoxy)phenyl]-3-hydroxymethylpyrrolidine, methyl 4-[1-[4-(4-tert-butylphenoxy)phenyl]pyrrolidin-3-yl]methoxybenzoate, 4-[1-[4-(4-tert-butylphenoxy)phenyl]pyrrolidin-3-yl]methoxybenzoic acid, 1-[4-(4-chlorophenoxy)phenyl]-3-hydroxymethylpyrrolidine, methyl 4-[1-[4-(4-chlorophenoxy)phenyl]pyrrolidin-3-yl]methoxybenzoate, 4-[1-[4-(4-chlorophenoxy)phenyl]pyrrolidin-3-yl]methoxybenzoic acid, 1-(4-chlorophenyl)-3-hydroxymethylpiperidine, methyl 4-[1-(4-chlorophenyl)piperidin-3-yl]methoxybenzoate, 4-[1-(4-chlorophenyl)piperidin-3-yl]methoxybenzoic acid, methyl 4-[1-(4-methanesulfonyloxyphenyl)-2-pyrrolidon-4-yl]methoxybenzoate, 4-[1-(4-methanesulfonyloxyphenyl)-2-pyrrolidon-4-yl]methoxybenzoic acid, methyl 4-[1-(4-ethanesulfonyloxyphenyl)-2-pyrrolidon-4-yl]methoxybenzoate, 4-[1-(4-ethanesulfonyloxyphenyl)-2-pyrrolidon-4-yl]methoxybenzoic acid, methyl 4-[1-(4-n-propanesulfonyloxyphenyl)-2-pyrrolidon-4-yl]methoxybenzoate, 4-[1-(4-n-propanesulfonyloxyphenyl)-2-pyrrolidon-4-yl]methoxybenzoic acid, methyl 4-[1-(4-n-butanesulfonyloxyphenyl)-2-pyrrolidon-4-yl]methoxybenzoate, 4-[1-(4-n-butanesulfonyloxyphenyl)-2-pyrrolidon-4-yl]methoxybenzoic acid, methyl 4-[1-(4-benzenesulfonyloxyphenyl)-2-pyrrolidon-4-yl]methoxybenzoate, 4-[1-(4-benzenesulfonyloxyphenyl)-2-pyrrolidon-4-yl]methoxybenzoic acid, methyl 4-[1-[4-(4-chlorobenzenesulfonyl)oxyphenyl]-2-pyrrolidon-4-yl]methoxybenzoate, 4-[1-[4-(4-chlorobenzenesulfonyl)oxyphenyl]-2-pyrrolidon-4-yl]methoxybenzoic acid, 1-(4-isobutyrylaminophenyl)-5-oxo-3-pyrrolidinecarboxylic acid, methyl 1-(4-isobutylaminophenyl)-5-oxo-3-pyrrolidinecarboxylate, 1-(4-isobutyrylaminophenyl)-4-hydroxymethyl-2-pyrrolidone, methyl 4-[1-(4-isobutylaminophenyl)-2-pyrrolidon-4-yl]methoxybenzoate, 4-[1-(4-isobutyrylaminophenyl)-2-pyrrolidon-4-yl]methoxybenzoic acid, 1-(4-pivaloylaminophenyl)-5-oxo-3-pyrrolidinecarboxylic acid, methyl 1-(4-pivaloylaminophenyl)-5-oxo-3-pyrrolidinecarboxylate, 1-(4-pivaloylaminophenyl)-4-hydroxymethyl-2-pyrrolidone, methyl 4-[1-(4-pivaioylaminophenyl)-2-pyrrolidon-4-yl]methoxybenzoate, 4-[1-(4-pivaloylaminophenyl)-2-pyrrolidon-4 -yl]methoxybenzoic acid, 1-(4-acetylaminophenyl)-5-oxo-3-pyrrolidinecarboxylic acid, methyl 1-(4-acetylaminophenyl)-5-oxo-3-pyrrolidinecarboxylate, 1-(4-acetylaminophenyl)-4-hydroxymethyl-2-pyrrolidone, methyl 4-[1-(4-acetylaminophenyl)-2-pyrrolidon-4-yl]methoxybenzoate, 4-[1-(4-acetylaminophenyl)-2-pyrrolidon-4-yl]methoxybenzoic acid, 1-(4-benzoylaminophenyl)-5-oxo-3-pyrrolidinecarboxylic acid, methyl 1-(4-benzoylaminophenyl)-5-oxo-3-pyrrolidinecarboxylate, 1-(4-benzoylaminophenyl)-4- hydroxymethyl-2-pyrrolidone, methyl 4-[1-(4-benzoylaminophenyl)-2-pyrrolidon-4-yl]methoxybenzoate, 4-[1-(4-benzoylaminophenyl)-2-pyrrolidon-4-yl]methoxybenzoic acid, 1-(2,4-dimethoxyphenyl)-5-oxo-3-pyrrolidinecarboxylic acid, methyl 1-(2,4-dimethoxyphenyl)-5-oxo-3-pyrrolidinecarboxylate, 1-(2,4-dimethoxyphenyl)-4-hydroxymethyl-2-pyrrolidone, methyl 4-[1-(2,4-dimethoxyphenyl)-2-pyrrolidon-4-yl]methoxybenzoate, 4-[1-(2,4-dimethoxyphenyl)-2-pyrrolidon-4-yl]methoxybenzoic acid, 1-(3,4-dimethoxyphenyl)-5-oxo-3-pyrrolidinecarboxylic acid, methyl 1-(3,4-dimethoxyphenyl)-5-oxo-3-pyrrolidinecarboxylate, 1-(3,4-dimethoxyphenyl)-4-hydroxymethyl-2-pyrrolidone, methyl 4-[1-(3,4-dimethoxyphenyl)-2-pyrrolidon-4-yl]methoxybenzoate, 4-[1-(3,4-dimethoxyphenyl)-2-pyrrolidon-4-yl]methoxybenzoic acid, 1-(2,5-dimethoxyphenyl)-5-oxo-3-pyrrolidinecarboxylic acid, methyl 1-(2,5-dimethoxyphenyl)-5-oxo-3-pyrrolidinecarboxylate, 1-(2,5-dimethoxyphenyl)-4-hydroxymethyl-2-pyrrolidone, methyl 4-[1-(2,5-dimethoxyphenyl)-2-pyrrolidon-4-yl]methoxybenzoate, 4-[1-(2,5-dimethoxyphenyl)-2-pyrrolidon-4-yl]methoxybenzoic acid, methyl 4-[1-(4-aminophenyl)-2-pyrrolidon-4-yl]methoxybenzoate, 4-[1-(4-aminophenyl)-2-pyrrolidon-4-yl]methoxybenzoic acid, methyl 1-(4-allyloxyphenyl)-5-oxo-3-pyrrolidinecarboxylate, 1-(4-allyloxyphenyl)-4-hydroxymethyl-2-pyrrolidone, methyl 4-[1-(4-allyloxyphenyl)-2-pyrrolidon-4-yl]methoxybenzoate, 4-[1-(4-allyloxyphenyl)-2-pyrrolidon-4-yl]methoxybenzoic acid, methyl 1-(4-metallyloxyphenyl)-5-oxo-3-pyrrolidinecarboxylate, 1-(4-metallyloxyphenyl)-4-hydroxymethyl-2-pyrrolidone, methyl 4-[1-(4-metaallyloxyphenyl)-2-pyrrolidon-4-yl]methoxybenzoate, 4-[1-(4-metallyloxyphenyl)-2-pyrrolidon-4-yl]methoxybenzoic acid, methyl 1-[4-(2-benzyloxyethoxy)phenyl]-5-oxo-3-pyrrolidinecarboxylate, 1-[4-(2-benzyloxyethoxy)phenyl]-4-hydroxymethyl-2-pyrrolidone, methyl 4-[1-[4-(2-benzyloxyethoxy)phenyl]-2-pyrrolidon-4-yl]methoxybenzoate, 4-[1-[4-((2-enzyloxyethoxy)phenyl]-2-pyrrolidon-4-yl]methoxybenzoic acid, methyl 4-[1-[4-(2-hydroxyethoxy)phenyl]-2-pyrrolidon-4-yl]methoxybenzoate, 4-[1-[4-(2-hydroxyethoxy)phenyl]-2-pyrrolidon-4-yl]methoxybenzoic acid, methyl 4-[1-(4-isobutoxyphenyl)-2-pyrrolidon-4-yl]methoxybenzoate, 4-[1-(4-isobutoxyphenyl)-2-pyrrolidon-4-yl]methoxybenzoic acid, methyl 4-[1-(4-isopentyloxyphenyl)-2-pyrrolidon-4-yl]methoxybenzoate, 4-[1-(4-isopentyloxyphenyl)-2-pyrrolidon-4-yl]methoxybenzoic acid, methyl 4-[1-(4-n-pentyloxyphenyl)-2-pyrrolidon-4-yl]methoxybenzoate, 4-[1-(4-n-pentyloxyphenyl)-2-pyrrolidon-4-yl]methoxybenzoic acid, methyl 4-[1-(4-n-hexyloxyphenyl)-2-pyrrolidon-4-yl]methoxybenzoate, 4-[1-(4-n-hexyloxyphenyl)-2-pyrrolidon-4-yl]methoxybenzoic acid, methyl 4-[1-[4-(4-methoxybenzyloxy)phenyl]-2-pyrrolidon-4-yl]methoxybenzoate, 4-[1-[4-(4-methoxybenzyloxy)phenyl]-2-pyrrolidon-4-yl]methoxybenzoic acid, methyl 4-[1-(4-cyclopentyloxyphenyl)-2-pyrrolidon-4-yl]methoxybenzoate, 4-[1-(4-cyclopentyloxyphenyl)-2-pyrrolidon-4-yl]methoxybenzoic acid, methyl 4-[1-(4-cyclohexylmethoxyphenyl)-2-pyrrolidon-4-yl]methoxybenzoate, 4-[1-(4-cyclohexylmethoxyphenyl)-2-pyrrolidon-4-yl]methoxybenzoic acid, methyl 4-[1-[4-(2-methanesulfonyloxyethoxy)phenyl]-2-pyrrolidon-4-yl]methoxybenzoate, methyl 4-[1-[4-[2-(1-imidazolyl)ethoxy]phenyl]-2-pyrrolidon-4-yl]methoxybenzoate, 4-[1-[4-[2-(1-imidazolyl)ethoxy]phenyl]-2-pyrrolidon-4-yl]methoxybenzoic acid, methyl 4-[1-(4-bromomethylphenyl)-2-pyrrolidon-4-yl]methoxybenzoate, methyl 4-[1-[4-(1-imidazolyl)methylphenyl]-2-pyrrolidon-4-yl]methoxybenzoate, 4-[1-[4-(1-imidazolyl)methylphenyl]-2-pyrrolidon-4-yl]methoxybenzoic acid, methyl 4-[1-(4-tert-butoxyphenyl)-2-pyrrolidon-4-yl]methoxybenzoate, 4-[1-(4-tert-butoxyphenyl) -2-pyrrolidon-4-yl]methoxybenzoic acid, methyl 4-[1-[4-(2-hydroxy-2-methylpropoxy)phenyl]-2-pyrrolidon-4-yl]methoxybenzoate, 4-[1-[4-(2-hydroxy-2-methylpropoxy)-phenyl]-2-pyrrolidon-4-yl]methoxybenzoic acid, 4-[1-[4-(2-hydroxycyclohexyloxy)phenyl]-2-pyrrolidon-4-yl]methoxybenzoic acid, 4-[1-[4-(2-hydroxycyclopentyloxy)phenyl]-2-pyrrolidon-4-yl]methoxybenzoic acid, methyl 4-[1-[4-(1-hydroxycyclohexan-1-yl)methoxyphenyl]-2-pyrrolidon-4-yl]methoxybenzoate, 4-[1-[4-(1-hydroxycyclohexan-1-yl)methoxyphenyl]-2-pyrrolidon-4-yl]methoxybenzoic acid, methyl 4-[1-[4-(1-hydroxycyclopentan-1-yl)methoxyphenyl]-2-pyrrolidon-4-yl]methoxybenzoate, 4-[1-[4-(1-hydroxycyclopentan-1-yl)methoxyphenyl]-2-pyrrolidon-4-yl]methoxybenzoic acid, methyl 4 -[1-[4-(3,4,5-trimethoxybenzyloxy)-phenyl]-2-pyrrolidon-4-yl]methoxybenzoate and 4-[1-[4-(3,4,5-trimethoxybenzyloxy)phenyl]-2-pyrrolidon-4-yl]methoxybenzoic acid.

In the present invention, particularly preferred examples of the compound as the phenylcarboxylic acid derivative of the formula (1) include methyl 4-[1-(4-n-poropylphenyl)-2-pyrrolidon-4-yl]methoxybenzoate, 4-[1-(4-n-propylphenyl)-2-pyrrolidon-4-yl]methoxybenzoic acid, methyl 4-[1-(4-n-butylphenyl)-2-pyrrolidon-4-yl]methoxybenzoate, 4-[1-(4-n-butylphenyl)-2-pyrrolidon-4-yl]methoxybenzoic acid, methyl 4-[1-(4-tert-butylphenyl)-2-pyrrolidon-4-yl]methoxybenzoate, 4-[1-(4-tert-butylphenyl)-2-pyrrolidon-4-yl]methoxybenzoic acid, methyl 4-[1-(4-n-pentylphenyl)-2-pyrrolidon-4-yl]methoxybenzoate, 4-[1-(4-n-pentylphenyl)-2-pyrrolidon-4-yl]methoxybenzoic acid, methyl 4-[1-(4-n-hexylphenyl)-2-pyrrolidon-4-yl]methoxybenzoate, 4-[1-(4-n-hexylphenyl)-2-pyrrolidon-4-yl]methoxybenzoic acid, methyl 4-[1-(4-cyclohexylphenyl)-2-pyrrolidon-4-yl]methoxybenzoate, 4-[1-(4-cyclohexylphenyl)-2-pyrrolidon-4-yl]methoxybenzoic acid, methyl 4-[1-(3,5-dimethylphenyl)-9-pyrrolidon-4-yl]methoxybenzoate, 4-[1-(3,5-dimethyiphenyl)-2-pyrrolidon-4-yl]methoxybenzoic acid, methyl 4-[1-(2,5-dimethylphenyl)-2-pyrrolidon-4-yl]methoxybenzoate, 4-[1-(2,5-dimethylphenyl)-2-pyrrolidon-4-yl]methoxybenzoic acid, methyl 4-[1-(2,4-dimethylphenyl)-2-pyrrolidon-4-yl]methoxybenzoate, 4-[1-(2,4-dimethylphenyl) -2-pyrrolidon-4-yl]methoxybenzoic acid, methyl 4-[1-(4-ethylphenyl)-2-pyrrolidon-4-yl]methoxybenzoate, 4-[1-(4-ethylphenyl)-2-pyrrolidon-4-yl]methoxybenzoic acid, methyl 4-[1-(4-isopropylphenyl)-2-pyrrolidon-4-yl]methoxybenzoate or 4-[1-(4-isopropylphenyl)-2-pyrrolidon-4-yl]methoxybenzoic acid. Among them, the (R)-(−) form, (S)-(+) form or racemic form of 4-[1-(4-tert-butylphenyl)-2-pyrrolidon-4-yl]methoxybenzoic acid or methyl ester thereof is preferred, with the (S)-(+) form or racemic form of 4-[1-(4-tert-butylphenyl)-2-pyrrolidon-4-yl]methoxybenzoic acid being most preferred.

The phenylcarboxylic acid derivatives represented by the formula (1) can be prepared in accordance with the method described in, for example, Japanese Patent Application Laid-Open No. Hei 3-275666 or International Patent Application Laid-Open No. WO94/06767, with the preparation in accordance with International Patent Application Laid-Open No. WO94/06767 being preferred.

The Lp(a) lowering agent and apo(a) formation suppressing agent according to the present invention are available by formulating the phenylcarboxylic acid derivative of the formula (a) or salt thereof into an ordinary form of a pharmaceutical preparation. The pharmaceutical preparation can be prepared using a conventional diluent or excipient such as filler, extender, binder, humectant, disintegrator, surfactant, diluent, excipient and/or the like. The pharmaceutical preparation can be selected from various forms according to the purpose of the treatment. Typical examples include tablets, pills, powders, solutions, suspensions, emulsions, granules, capsules, suppositories, injections (in the form of solutions, suspensions or the like) and ointments. Upon formulation into tablets, usable examples of the carrier include excipients such as lactose, sucrose, sodium chloride, glucose, urea, starch, calcium carbonate, kaolin, crystalline cellulose and silicic acid; binders such as water, ethanol, propanol, simple syrup, glucose solution, starch solution, gelatin solution, carboxymethyl cellulose, shellac, methylcellulose, potassium phosphate and polyvinylpyrrolidone; disintegrants such as dried starch, sodium alginate, agar powder, laminaran powder, sodium bicarbonate, calcium carbonate, polyoxyethylene sorbitan fatty acid esters, sodium lauryl sulfate, stearic monoglyceride, starch and lactose; disintegration inhibitors such as sucrose, stearin, cacao butter and hydrogenated oils; absorption promoters such as quaternary ammonium salts and lauryl sodium sulfate; humectants such as glycerin and starch; adsorbents such as starch, lactose, kaolin, bentonite and colloidal silicic acid; and lubricants such as talc, stearate salts, boric acid powder and polyethylene glycol.

In the case of tablets, they can be formed, as needed, into tablets applied with a conventional coating, for example, into sugar coated tablets, gelatin coated tablets, enteric coated tablets or film coated tablets; or they can be formed into double layer tablets or multiple layer tablets. Upon formation into pills, carriers such as excipients, e.g., glucose, lactose, starch, cacao butter, hydrogenated vegetable oils, kaolin and talc; binders, e.g., gum arabic powder, tragacanth powder, gelatin and ethanol; and disintegrators, e.g., laminaran and agar can be employed. Upon forming suppositories, carriers such as polyethylene glycol, cacao butter, higher alcohols, esters of higher alcohols, gelatin and semi-synthetic glyceride can be used. Capsules can be formulated in a conventional manner by mixing the compound of the present invention with the above-exemplified various carrier and then filling the resultant mixture in hard gelatin capsules, soft capsules or the like. When the compound of the present invention is formulated as injections, solutions, emulsions or suspensions are sterilized and are preferably made isotonic with blood. Upon formulation into such forms, it is possible to use, as a diluent, water, aqueous solution of lactic acid, ethyl alcohol, propylene glycol, ethoxylated isostearyl alcohol, polyoxylated isostearyl alcohol, polyoxyethylene sorbitan fatty acid ester or the like. In this case, the pharmaceutical preparations may also contain sodium chloride, glucose or glycerin in an amount enough to make them isotonic and may also contain an ordinarily employed solubilizer, buffer or soothing agent. One or more of colorants, preservatives, perfumes, corrigents, sweeteners and other drugs can be incorporated in pharmaceutical preparations as needed. Upon formation into paste, cream or gel, white vaseline, paraffin, glycerin, cellulose derivative, polyethylene glycol, silicon, bentonite or the like can be used as a diluent.

No particular limitation is imposed on the content of the phenylcarboxylic acid derivative of the formula (1) or salt thereof to be incorporated in the Lp(a) lowering agent or apo(a) formation suppressing agent according to the present invention. Its content can be chosen suitably from a wide range. In general, however, it is desired to incorporate the derivative or salt thereof in amount of about 1–70 wt. % in each pharmaceutical preparation.

There is no particular limitation imposed on the manner of administration of the Lp(a) lowering agent or apo(a) formation suppressing agent according to the present invention insofar as the effective dose is administered to a patient having a high Lp(a) or apo(a) level in blood. Each preparation can be administered to a patient in a manner commensurate with the form of the preparation or the age, sex, other conditions or the seriousness of disease of the patient. For example, tablets, pills, solutions, suspensions, emulsions, granules and capsules can be administered orally. Injections can be intravenously administered either singly or as mixtures with an ordinary fluid replacement such as a glucose solution or an amino acid solution. These injections can also be administered singly by an intramuscular, subcutaneous or intraperitoneal route. Suppositories can be rectally administered.

The dose of the Lp(a) lowering agent or apo(a) formation suppressing agent according to the present invention can be suitably chosen depending on the manner of its administration and the age, sex, other conditions and the seriousness of disease of each patient. In general, it is however desired to administer the phenylcarboxylic acid derivative of the formula (1) or salt thereof in an amount of about 0.5–200 mg/kg/day, particularly about 2 to 50 mg/kg/day in one to four portions.

The pharmaceutical of the present invention is administered to a patient having a high Lp(a) level in blood. Particularly preferred is the administration to a patient whose serum cholesterol, neutral fat and HDL-cholesterol levels are normal but the Lp(a) level in blood is high.

EXAMPLES

The present invention will hereinafter be described more specifically by examples. It should however be borne in mind that the present invention is not limited to or by them.

Example 1

An injection was prepared according to the composition as shown in Table 1. Described specifically, methyl (R)-(-)-4-[1-(4-tert-butylphenyl)-2-pyrrolidon-4-yl]methoxybenzoate (Compound 1) and glucose were dissolved in distilled water. The resulting solution was poured in a 5 mL ampoule, followed by purging with nitrogen and sterilization at 121° C. for 15 minutes under pressure, whereby an injection was obtained.

TABLE 1

| | |
|---|---|
| Methyl (R)-(-)-4-[1-(4-tert-butylphenyl)-2-pyrrolidon-4-yl]methoxybenzoate (Compound 1) | 200 mg |
| Glucose | 250 mg |
| Distilled water for injection | q.s. |
| Total amount | 5 ml |

Example 2

A film coated tablet was prepared according to the composition as shown in Table 2. Described specifically, methyl (S)-(+)-4-[1-(4-tert-butylphenyl)-2-pyrrolidon-4-yl]methoxybenzoate (Compound 2), Avicel, corn starch and magnesium stearate were mixed and abraded, followed by tableting by a punch (R: 10 mm) for sugar coating. The resulting tablet was applied with a film coating agent composed of TC-5, polyethylene glycol-6000, castor oil and ethanol, whereby a film coated tablet was obtained.

TABLE 2

| | |
|---|---|
| Methyl (S)-(+)-4-[1-(4-tert-butylphenyl)-2-pyrrolidon-4-yl]methoxybenzoate (Compound 2) | 100 g |
| Avicel (trade name; product of Asahi Chemical Industry Co., Ltd.) | 40 g |
| Corn starch | 30 g |
| Magnesium stearate | 2 g |
| TC-5 (trade name; hydroxypropylmethyl cellulose, product of Shin-Etsu Chemical Co., Ltd.) | 10 g |
| Polyethylene glycol 6000 | 3 g |
| Castor oil | 40 g |
| Ethanol | 40 g |

Example 3

An ointment was prepared according to the composition as shown in Table 3. Described specifically, white beeswax was liquefied by heating, followed by the addition of 4-[1-(4-tert-butylphenyl)-2-pyrrolidon-4-yl]methoxybenzoic acid (Compound 3), purified lanolin and white vaseline. After the resulting mixture was liquefied by heating, it was stirred until the beginning of the solidification, whereby an ointment was obtained.

TABLE 3

| | |
|---|---|
| 4-[1-(4-tert-butylphenyl)-2-pyrrolidon-4-yl]methoxybenzoic acid (Compound 3) | 2 g |
| Purified lanolin | 5 g |
| White beeswax | 5 g |
| White vaseline | 88 g |
| Total amount | 100 g |

Example 4

A suppository was prepared in a conventional manner by using the composition as shown in Table 4.

TABLE 4

| | |
|---|---|
| (S)-(+)-4-[1-(4-tert-butylphenyl)-2-pyrrolidon-4-yl]methoxybenzoic acid (Compound 4) | 50 mg |
| Witepsol W-35 (registered trademark; a mixture of mono-, di- and tri-glycerides of saturated fatty acids ranging from lauric acid to stearic acid, product of Dynamite Nobel Corp.) | 1400 mg |

Test 1

Test on suppression of apo(a) gene expression

This test was carried out in accordance with the method described in "BIOCHEMICAL AND BIOPHYSICAL RESEARCH COMMUNICATIONS 227, 570–575(1966) ARTICLE No. 1547". Described specifically, 2 $\mu$g/mL of an apo(a) gene (1441 base pairs) separated from the blood of normal volunteers was introduced into HepG2 cells ($2 \times 10^5$ cells/mL), followed by culturing for 16 hours. Compound 4 was dissolved in DMSO (dimethylsulfoxide) to give a final concentration of 2 $\mu$M, to which the cultured cells were added. After culturing for further 48 hours, the expression of an apo(a) gene was measured regarding it as luciferases reaction and therefore, using luciferases assay system (Picagene) of Toyo Ink Mfg. Co., Ltd. for the analysis of gene expression. Namely, the cultured HepG2 cells were dissolved in a liquid to dissolve them therein. The resulting solution was centrifuged to obtain a supernatant. To 200 $\mu$l of the resulting supernatant was added 100 $\mu$l of a picagene substrate, followed by mixing for 15 seconds. The luminescence was measured by a chemo-bioluminescence measuring device (Luminoscan RS) of Dainippon Pharmaceutical Co., Ltd. and expression ratio of an apo(a) gene was determined. The expression ratio of an apo(a) gene was calculated from the ratio to the luminescence of a group (control group) to which the same amount of DMSO had been added. As comparative compounds, pravastatin (HMG-COA reductase inhibitor, sterol synthesis inhibitor) and bezafibrate (fibrate series medicament, antihyperlipoproteinemic) were treated in a similar manner and provided for the test. The results are shown in Table 5.

TABLE 5

| Test compound | Expression ratio (%) of apo(a) gene |
|---|---|
| Compound 4 | −24 |
| Pravastatin | +27 |
| Bezafibrate | +3 |

From Table 5, it has been confirmed that Compound 4 which was an effective ingredient of the present invention exhibited excellent effects for suppressing the expression of an apo(a) gene, while both of pravastatin and bezafibrate, on the contrary, reinforced the expression of the apo(a) gene.

Test 2

A test on lowering of the Lp(a) level

Crab-eating monkeys (male, 2.4 to 3.9 kg in weight) were reared in groups, each group consisting of 5 monkeys. Compound 4 was suspended in a 0.5%, HPMC (hydroxypropylmethyl cellulose) solution in an amount of 30 mg/5 mL, whereby the test compound was prepared. To the specimen-administered group, the test compound was orally administered at a dose of 30 mg/kg. At the starting time of administration and three weeks after administration, the Lp(a) level in the blood of the tested animals was measured. For the measurement, a kit ("Immunosearch Lp(a) TIA") commercially available from Cosmo Bio Co., Ltd. was employed. Namely, according to the procedure as indicated in the kit, the measurement was carried out by adding 256 $\mu$l of a phosphate buffer to 7 $\mu$l of the serum and then adding the goat anti-human Lp(a) serum to the resulting mixture. For the measurement, a biochemical automatic analyzer ("Hitachi 7170"; product of Hitachi Ltd.) was employed. As a comparative compound, pravastatin and bezafibrate were treated similarly and provided for the test. From the measuring results, a changing ratio (%) of the Lp(a) level at the starting time of administration relative to that three weeks after the administration was determined with regards to each of the monkeys and the average value was expressed as an Lp(a) lowering ratio. The results are shown in Table 6.

TABLE 6

| Test compound | Changing ratio (%) of Lp(a) |
|---|---|
| Compound 4 | −33 |
| Pravastatin | +35 |
| Bezafibrate | +8 |

From Table 6, it has been confirmed that Compound 4 exhibited excellent Lp(a) lowering effects, but pravastatin and bezafibrate each increased the Lp(a) level.

Test 3

Acute toxicity test

After 7-month old beagles (male, each group consisting of 2 beagles) were fasted for 16 hours, Compound 4 suspended in a 0.5%, HPMC solution was orally administered at a dose of 2000 mg/kg. As a result of observation, neither death case nor serious side effects were recognized.

Capability of Exploitation in Industry

The Lp(a) lowering agent and apo(a) formation suppressing agent according to the present invention are capable of significantly reducing the Lp(a) level and also the level of apo(a) which is a component of Lp(a), are almost free from side effects and exhibit effects at a low dose. Such Lp(a) lowering agent and apo(a) formation suppressing agent are particularly useful for the case where a patient tends to cause arteriosclerotic diseases in spite of lacking the factor of hypercholesterolemia, diabetes, hypertension or the like. Moreover, they are useful as a remedy or preventive for Buerger's disease or remedy or preventive for reconstriction after anti-thrombosis or PTCA.

What is claimed is:

1. A method of treating diseases exhibiting a high blood Lp(a) level, which comprises administering a phenylcarboxylic acid derivative represented by the following formula (1):

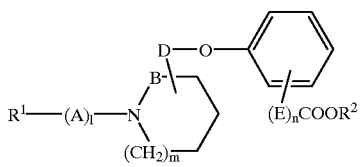

(wherein, $R^1$ represents a phenyl group which may have a substituent, A represents a lower alkylene or lower alkyleneoxy group, B represents a methylene or carbonyl group, D represents a lower alkylene group, E represents a lower alkylene or lower alkenylene group, $R^2$ represents a hydrogen atom or a lower alkyl group and l, m and n each stands for 0 or 1) or salt thereof.

2. The method according to claim 1, wherein $R^1$ represents a phenyl group substituted by a lower alkyl group, B represents a carbonyl group, D represents a lower alkylene group and l, m and n each stands for 0.

3. The method according to claim 2, wherein $R^1$ represents a phenyl group substituted by a tert-butyl group and D represents a methylene group.

4. The method according to any one of claims 1 to 3, wherein the phenylcarboxylic acid derivative is 4-[1-(4-tert-butylphenyl)-2-pyrrolidon-4-yl]methoxybenzoic acid.

5. The method according to any one of claims 1 to 3, wherein the phenylcarboxylic acid derivative is S-(+)-4-[1-(4-tert-butylphenyl)-2-pyrrolidon-4-yl]methoxybenzoic acid.

6. The method according to any one of claims 1 to 3, wherein the diseases exhibiting a high blood Lp(a) level are diseases wherein each of the blood cholesterol, neutral fat and HDL-cholesterol levels falls within a normal range but the blood Lp(a) level is high.

7. A method of treating a patient exhibiting a high blood apolipoprotein (a) level, which comprises administering a phenylcarboxylic acid derivative represented by the following formula (1):

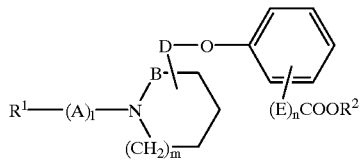

(wherein, $R^1$ represents a phenyl group which may have a substituent, A represents a lower alkylene or lower alkyleneoxy group, B represents a methylene or carbonyl group, D represents a lower alkylene group, E represents a lower alkylene or lower alkenylene group, $R^2$ represents a hydrogen atom or a lower alkyl group and l, m and n each stands for 0 or 1) or salt thereof.

8. The method according to claim 7, wherein $R^1$ represents a phenyl group substituted by a lower alkyl group, B represents a carbonyl group, D represents a lower alkylene group and l, m and n each stands for 0.

9. The method according to claim 8, wherein $R^1$ represents a phenyl group substituted by a tert-butyl group and D represents a methylene group.

10. The method according to any one of claims 7 to 9, wherein the phenylcarboxylic acid derivative is 4-[1-(4-tert-butylphenyl)-2-pyrrolidon-4-yl]methoxybenzoic acid.

11. The method according to any one of claims 7 to 9, wherein the phenylcarboxylic acid derivative is S-(+)-4-[1-(4-tert-butylphenyl)-2-pyrrolidon-4-yl]methoxybenzoic acid.

12. The method according to claim 6, wherein the phenylcarboxylic acid derivative is 4-[1-(4-tert-butylphenyl)-2-pyrrolidon-4-yl]methoxybenzoic acid.

13. The method according to claim 6, wherein the phenylcarboxylic acid derivative is S-(+)-4-[1-4-tert-butylphenyl)-2-pyrrolidon-4-yl]methoxybenzoic acid.

* * * * *